(12) United States Patent  (10) Patent No.: US 8,716,005 B2
Abeygunaratne  (45) Date of Patent: May 6, 2014

(54) METHOD AND DEVICE TO PROBE A MEMBRANE BY APPLYING AN IN-PLANE ELECTRIC FIELD

(75) Inventor: Thusara Sugat Chandra Abeygunaratne, Stow, OH (US)

(73) Assignee: Kent State University, Kent, OH (US)

( * ) Notice: Subject to any disclaimer, the term of this patent is extended or adjusted under 35 U.S.C. 154(b) by 175 days.

(21) Appl. No.: 12/834,328

(22) Filed: Jul. 12, 2010

(65) Prior Publication Data

US 2010/0281586 A1 Nov. 4, 2010

Related U.S. Application Data

(62) Division of application No. 11/851,633, filed on Sep. 7, 2007, now Pat. No. 7,803,588.

(60) Provisional application No. 60/824,817, filed on Sep. 7, 2006.

(51) Int. Cl.
*C12M 1/00* (2006.01)
*C12Q 1/68* (2006.01)
*G01N 33/53* (2006.01)
*C12N 13/00* (2006.01)
*G01N 27/00* (2006.01)

(52) U.S. Cl.
USPC ....... 435/283.1; 435/6.1; 435/7.2; 435/173.4; 422/82.01; 422/82.02

(58) Field of Classification Search
USPC .......... 435/6.1, 7.2, 173.4, 283.1; 422/82.01, 422/82.02
See application file for complete search history.

(56) References Cited

U.S. PATENT DOCUMENTS

| | | | |
|---|---|---|---|
| 5,321,533 A | 6/1994 | Kumar | |
| 5,670,322 A | 9/1997 | Eggers et al. | |
| 6,228,326 B1 | 5/2001 | Boxer et al. | |
| 6,627,396 B1 | 9/2003 | Swanson et al. | |
| 6,932,893 B2 | 8/2005 | Bech et al. | |
| 2002/0164777 A1 | 11/2002 | Kelly et al. | |
| 2004/0214312 A1 | 10/2004 | Tyvoll et al. | |
| 2005/0011256 A1* | 1/2005 | Hoh | 73/105 |
| 2006/0216740 A1 | 9/2006 | Edman et al. | |

OTHER PUBLICATIONS

Wegener et al, Recovery of Adherent Cells after In Situ Electroporation Monitored Electrically, 2002, BioTechniques, 33, 348-357.*
Groves, Jay T., et al., "Micropatterning fluid lipid bilayers on solid supports," Science, vol. 275, Jan. 31, 1997, pp. 651-653.

(Continued)

*Primary Examiner* — Narayan Bhat
(74) *Attorney, Agent, or Firm* — Fay Sharpe LLP (57) ABSTRACT

The present invention disposes a membrane between two electrical conductive walls having a height at least as great as the thickness of the membrane. The conductive walls are fabricated on an electrically insolative chip base. The chip base has one or more through hole between the electrically conducting walls. The chip is placed inside a container having a well below the through hole of the electrically insolative base. At least one passageway extends from the well to the periphery of the container. This invention probes changes of the membrane as an in-plane electric field is applied between the conductive walls. The well may include various compounds while other compounds can be placed in contact with the top of the membrane. The passageways are used to introduce substances into and out of the well.

21 Claims, 9 Drawing Sheets

(56) References Cited

OTHER PUBLICATIONS

Boxer, Steven G., "Molecular transport and organization in supported lipid membranes," Current Opinion in Chemical Biology 2000, 4:704-709.

Pantoja, Rigo, et al., "Bilayer reconstitution of voltage-dependent ion channels using a microfabricated silicon chip," Biophysical Journal, vol. 81, Octover 2001, pp. 2389-2394.

Abeygunaratne, S., et al., "Evidence for uncorrelated tilted layer structure and electrically polarized bilayers in amphiphilic glycolipids," Physical Review E73, 011916 (2006), pp. 011916-1-011916-6.

Sackmann, E., "Supported membranes: scientific and practical applications," Science, New series, vol. 271, No. 5245 (Jan. 5, 1996), pp. 43-48.

Groves Jay, T., "Electric field-induced reorganization of two-component supported bilayer membranes," Proc. Natl. Acad. Sci. USA, vol. 94, pp. 13390-13395, Dec. 1997.

Filmore, David, "Breaching the blood-brain barrier," Modern Drug Discover, Jun. 2002, vol. 5, No. 6, pp. 22-24, 27.

Craighead, H., et al., "Applications: biotechnology, medicine, and healthcare," Nantechnology Research Directions: IWGN Workshop Report, Sep. 1999, Chapter 8, pp. 107-120, www.wtec.org/loyola/nano.IWGN.Research. Directions/chapter08.pdf.

Fernandez, J.M., "Cellular and molecular mechanics by atomic force microscopy: capturing the exocytotic fusion pore in vivo?", Proc. Natl. Acad. Sci. USA, Col. 94, pp. 9-10, Jan. 1997.

Nichii, Masayuki, et al., "Thermotropic liquid-crystalline peptide derivatives: oligo (glutamic acids) forming hydrogen-bonded columns," Org. Biomol. Chem., 2005, 3, pp. 875-880.

Catterall, William A., "Molecular properties of voltage-sensitive sodium channels," Ann. Rev. Biochem., 1986, 55:953-985.

Guy, H. Robert, et al., "Molecular model of the action potential sodium channel," Proc. Natl. Acad. Sci. USA, vol. 83, pp. 508-512, Jan. 1986.

Jiang, Youxing, et al., "The principle of gating charge movement in a voltage-dependent K+ channel," Nature, vol. 423, May 1, 2003, www.nature.com/nature, pp. 42-48.

Ahern, Christopher A., et al., "Stirring up controversy with a voltage sensor paddle," Trends in Neurosciences, vol. 27, No. 6, Jun. 6, 2004, pp. 303-307.

Bezanilla, Francisco, "The voltage sensor in voltage-dependent ion channels," Physiological Reviews, vol. 80, No. 2, Apr. 2000, pp. 555-592.

Vill, V., et al., "Thermotropic and lyotropic properties of long chain alkyl glycopyranosides, Part I: monosaccharide headgroups," Chemistry and Physics of Lipids, 104 (2000) pp. 75-91.

Jiang, Youxing, et al., X-ray structure of a voltage-dependent K+ channel,: Nature, vol. 423, May 1, 2003, www.nature.com/nature, pp. 33-41.

Singer, S.J., et al., "The fluid mosaic model of the structure of cell membranes," Science, vol. 175, pp. 720-731, 1972.

Leuchtag, H. Richard, "Fit of the dielectric anomaly of squid membrane near heat-block temperature to the ferroelectric Curie-Weiss law," Biophysical Chemistry 53 (1995) pp. 197-205.

Hodgkin, A.L., et al., "The effect of temperature on the electrical activity of the giant axon of the squid," J. Physiol. (1949) 109, pp. 240-249.

Armstrong, Clay M., et al., "Charge movement associated with the opening and closing of the activation gates of the Na channels," The Journal of General Physiology, vol. 63, 1974, pp. 533-552.

Neville, A.C., et al., "A biological system producing a self-assembling cholesteric protein liquid crystal," J. Cell Sci. 8, pp. 93-109 (1971).

Montal, M., et al., "Formation of biomolecular membranes from lipid monolayers and a study of their electrical properties," Proc. Natl. Acad. Sci. USA, vol. 69, No. 12, pp. 3561-3566, Dec. 1972.

Sigworth, F.J., "Voltage gating of ion channels," Quarterly Reviews of Biophysics 27, 1 (1993), pp. 1-40.

Chanda, Baron, et al., Gating charge displacement in voltage-gated ion channels involves limited transmembrane movement,: Nature, vol. 436, Aug. 11, 2005, pp. 852-856.

Asamoah, Osei Kwame, et al., "A fluorometric approach to local electric field measurements in a voltage-gated ion channel," Neuron, vol. 37, pp. 85-97, Jan. 9, 2003.

Cha, Albert, et al., "Atomic scale movement of the voltage-sensing region in a potassium channel measured via spectroscopy," Nature, vol. 402, Dec. 16, 1999, pp. 809-817.

Starace, Dorine M., et al., Voltage-dependent proton transport by the voltage sensor of the Shaker K+ channel,: Neuron, vol. 19, pp. 1319-1327, Dec. 1997.

Yang, Naibo, et al., Molecular basis of charge movement in a voltage-gated sodium channels,: Neuron, vol. 16, pp. 113-122, Jan. 1996.

Abeygunaratne, S., et al., "The active role of membrane lipids in opening and closing of ion channels," 25 pages, May 13, 2009.

Abeygunaratne, S., et al., "Tilted supramolecular structures of mphiphilic glycolipids in straight-core smectic C liquid crystals," 12 pages, May 13, 2009.

Chang, Geoffrey, et al., "Structure of the MscL homolog from mycrobacterium tuberculosis: a gated mechanosensitive ion channel," Science, vol. 282, Dec. 18, 1998, pp. 2221-2226.

Dutzler, Raimund, et al., "X-ray structure of ClC chloride channel at 3.0A reveals the molecular basis of anion selectivity," Nature, vol. 415, Jan. 17, 2002, pp. 287-294.

Ellens, Harma, et al., "Fusion of phosphatidylethanolamine-containing liposomes and mechanism of the [---] phase transition," Biochemistry, 1986, 25, pp. 4141-4147.

Glauner, K.S., et al., "Spectroscopic mapping of voltage sensor movement in the Shaker potassium channel," Nature, vol. 402, Dec. 16, 1999, pp. 813-817.

DeGennes, P.G., et al., "Magnetic field effects," The Physics of Liquid Crystals, 1993, pp. 116-120.

Wiki (http://lamp.tu-raz.ac.at/%7Ehadley/nanoscience/glossary.html), Printed Apr. 25, 2009.

Office Action dated Oct. 31, 2008 for U.S. Appl. No. 11/400,685, filed Apr. 7, 2006.

Final Office Action dated Apr. 28, 2009 for U.S. Appl. No. 11/400,685, filed Apr. 7, 2006.

Office Action dated Sep. 2, 2009 for U.S. Appl. No. 11/851,633, filed Sep. 7, 2007.

Final Office Action dated Feb. 17, 2010 for U.S. Appl. No. 11/851,633, filed Sep. 7, 2007.

Restriction Requirement dated Jun. 10, 2009 for U.S. Appl. No. 11/851,633, filed Sep. 7, 2007.

Restriction Requirement dated Jun. 23, 2008 for U.S. Appl. No. 11/400,685, filed Apr. 7, 2006.

\* cited by examiner

METHOD AND DEVICE TO PROBE A MEMBRANE BY APPLYING AN IN-PLANE ELECTRIC FIELD

CROSS-REFERENCE TO RELATED APPLICATION

This application is a Divisional of U.S. patent application Ser. No. 11/851,633, filed on Sep. 7, 2007, which claims the benefit of U.S. Provisional Application Ser. No. 60/824,817, filed on Sep. 7, 2006. This application also has the same inventorship as U.S. patent application Ser. No. 11/400,685, filed on Apr. 7, 2006. These applications are incorporated herein by reference in their entirety.

BACKGROUND OF THE INVENTION

The membrane of the biological cell, consisting of amphiphilic glycolipids, phospholipids, cholesterol and proteins, is the outermost boundary that separates the intracellular components from the extracellular environment and is involved in a wide variety of biological processes. It is semipermeable and capable of regulating what enters and exits the cell. The transport of substances in and out of the cell can take place with or without active participation of the cell membrane. The surface of the cell membrane anchors the cytoskeleton and the other molecules that activate or deactivate certain cell processes. Proteins embedded in the membrane act as selective channels for ions, receptors for information exchange between cells and organelles, and take part in activities such as immune response and cell adhesion. The membrane and the proteins carry out these functions mainly by changing their structure reversibly. How these structural changes take place and the molecular mechanisms behind them are at the forefront of life science research.

The structure of the generally accepted fluid mosaic model of the membrane is a self assembling two dimensional smectic liquid crystalline amphiphilic lipid bilayer in which hydrophobic hydrocarbon chains are inside and hydrophilic polar headgroups are outside. However, recent studies show that cell membranes contain different structures or domains that can be classified as protein-protein complexes; lipid rafts, pickets and fences formed by the actin-based cytoskeleton; and other large stable structures, such as synapses or desmosomes.

The phase behavior of lipids in the membrane is known to be involved in cell fusion processes and membrane traffic, for example, during exocytosis or virus-cell fusion in the course of an infection. The propagation of action potential in nerve and muscle cell and retinal photoreceptors have been attributed to the ferroelectric properties arising from chiral building blocks. A Curie point and current-voltage hysteresis typical of ferroelectric substances have been observed in cell membranes. Temperature dependent current has been induced by laser in frog of ranvier suggesting a pyroelectric effect. Swelling of membranes in response to a voltage application, which indicates a piezoelectric effect, has been reported. It has been suggested that ferroelectricity may be common in cell components and a relationship between liquid crystalline ferroelectricity and nerve and muscle impulses has been predicted, but so far the possible origin of the ferroelectric structure in the cell membrane has not been demonstrated.

Both glycolipids and phospholipids contain polar (hydrophilic) head groups and apolar (hydrophobic) alkyl chains. They are quite similar in their molecular shape and phase behavior. They are amphotropic liquid crystals: they form thermotropic liquid crystalline phases in their pure form as the temperature is varied and lyotropic liquid crystalline phases in solvent as the concentration is varied. The length of the alkyl chain and the number of head groups determine the polymorphism in both thermotropic and lyotropic structures. They form smectic bilayers in water at a critical concentration of lipids. Lyotropic properties of both glycolipids and phospholipids have been extensively studied in the last decade but so far their thermotropic properties have not been assessed properly. The thermotropic form of membrane lipids, both phospholipids and glycolipids, presents a unique opportunity to investigate many of their physical especially electrical properties which are more difficult to study in aqueous systems. Most membrane lipids with two long alkyl chains form only a columnar phase in their pure form. A smectic phase of these membrane lipids can be induced by mixing them with amphiphilic lipids which form only a smectic phase, providing ideal systems to investigate structural and electrical properties of lipid bilayers.

Recently it was shown based on dielectric and X-ray diffraction studies, and optical microscopic observations that the glycolipid molecules are tilted in their bilayers in the smectic phase but the direction of the tilt is varied from one bilayer to the next. Large numbers of studied synthetic glycolipids with varying chemical structures exhibited quite similar behavior. The tilted supramolecular structures they from in both bent-core and straight-core liquid crystals also show that lipid molecules are tilted in the bilayers. The bilayers of tilted chiral glycolipid molecules are electrically polarized. It is also known that amphiphilic lipids form only one smectic phase in both thermotropic and lyotropic form. Since the smectic phase in thermotropic form of the amphiphilic lipids is similar or identical to their smectic phase in the lyotropic form, the amphiphilic lipid bilayers may be polarized even in the aqueous medium. Therefore, it is possible that the tilted lipids will give rise to ferroelectric domains in the biological cell membranes as well. As a result of in-plane anisotropy and ferroelectricity of the membrane, the lipid bilayer may play an active role in determining the excitable properties of the cell membrane.

Most proteins fold into unique three dimensional structures. The shape into which a protein naturally folds is known as its native state. There are four main protein structures known as primary, secondary, tertiary, and quaternary structures. In addition to the biochemical role of these main structures, proteins may shift between several related structures in performing their biological function. In the context of these functional rearrangements, these tertiary or quaternary structures are usually referred to as "conformations," and transitions between them are called conformational changes. For example, the binding of a substrate molecule to an enzyme results in such conformational changes in physical regions of the protein that participate in chemical catalysis. Discovering the tertiary and quaternary structure of protein complexes, can provide important clues about how the protein performs its function.

The main experimental methods of structure determination are X-ray crystallography and NMR spectroscopy, both of which can produce information at atomic resolution. At lower resolution, the cryo-electron microscopy is used to determine secondary structures of very large protein complexes such as virus coat proteins and amyloid fibers. A variant known as electron crystallography is also used in high-resolution studies in some cases, especially for two-dimensional crystals of membrane proteins. Solved structures are usually stored in the Protein Data Bank (PDB), a freely available resource from which structural data about thousands of proteins can be obtained in the form of Cartesian coordinates for each atom in the protein.

There are many more known gene sequences than there are solved protein structures. Further, the set of solved structures is biased toward those proteins that can be easily subjected to the experimental conditions required by one of the major structure determination methods. In particular, globular proteins are comparatively easy to crystallize in preparation for X-ray crystallography, which remains the oldest and most common structure determination technique. Membrane proteins, by contrast, are difficult to crystallize and are underrepresented in the PDB. Structural genomics initiatives have attempted to remedy these deficiencies by systematically solving representative structures of major fold classes. Protein structure prediction methods attempt to provide a means of generating a plausible structure for a protein whose structures have not been experimentally determined.

DISCLOSURE OF THE INVENTION

It is an object of the invention to provide a method to probe dynamic conformational changes and associated functions in the biological cell membrane and membrane proteins by applying an in-plane transverse electric field. As this method is not dictated by purification and re-crystallization of the proteins, the proteins can be probed in their native environment. The membrane can be extracted from a biological cell or can be formed synthetically by individual constituents of extracted from the biological cell membrane or by synthetic molecules. The proteins can be inserted into the membrane during and after the construction of the membrane. Subsequently, the membrane is subjected to the in-plane electric field and probing its structural changes coupled with the in-plane electric field.

It is a further object of the invention to provide a device with which the inventive method can be applied. The principle underlying both the method and the inventive device is based on the insight that when an alternating electric field is applied along the plane of the membrane, the in-plane electric field causes a structural transition in the constituent molecules of the membrane. Membrane proteins acquire unique structures in response to the strength and the frequency of the electric field and time evolution of these structural changes are observable in the extracellular part of the proteins. In addition, structural changes taking place in the intracellular part of the proteins can be determined by electrical characterizations. These dynamic structural changes may be related to the biological functions of the membrane. Time evolution of structural changes cannot be probed by X-ray or NMR measurements in real time. These molecular activities of the membrane now can be probed with the present invention in that the structural changes can be induced and controlled by an external electric field and probed using a number of microscopic and electrical measurements.

This invention relates to probing of the structural transitions of the membrane and the membrane proteins using electric current measurements, impedance gain phase analysis, raster scanning by atomic force microscope, and further characterization of the membrane with confocal microscopy, X-ray spectroscopy and NMR, but not limited to these tools.

This invention applies to all aspects of membranes and, in particular, to the structural functions of biological cell membranes including the biological sciences of the biological cell membrane, medical and clinical research of the biological cell membrane and diagnosis of diseases related to membrane and protein dysfunctions.

According to the invention, to apply an electric field in the plane of the membrane, the membrane is disposed between two electrodes forming a containment region of a nanometer scale parallel plate capacitor. One side of each electrode is, for example, about 5-10 nanometers ($1 \times 10^{-9}$ m or nm) high so that it is not less than the height of the membrane and, in particular, is approximately the same height as the membrane. The distance between the electrodes is, for example, about 3-10 micrometers ($1 \times 10^{-6}$ m or μm) which is suitable for a sufficiently large electric field. To enable access for probing, the membrane is positioned to have a well-defined configuration with the plane of the membrane being perpendicular to the sides of the electrodes. The following are advantageous conditions in which probing of the membrane is carried out:

1. The membrane should span the entire containment volume as exact as possible with the plane of the membrane laying perpendicular to the sides of the electrodes.
2. The insertion of any constituents of the membrane such as membrane proteins is possible at any stage of probing.
3. It is possible to bring extracellular and inner cellular materials into contact with each side of the membrane.
4. The surface of the membrane is advantageously accessible for probing devices such as a tip of the Atomic Force Microscope ("AFM"), a beam of light, a laser of the confocal microscope, and an X-ray beam, but not limited to these tools.

The conductive walls are fabricated on an electrically insulative base (e.g., made of silicon wafer) and can be parallel to each other and perpendicular to the base. In view of the nanometer scale height of the conductive walls and the wafer they are fabricated on, this can be called a nanochip. Non-conductive walls surrounding the conducting walls can be fabricated on the chip base. Two electrically conductive pads extending from each of the conductive walls are fabricated on the chip base. The electrically conducting walls and pads can be coated with a thin non-conductive layer. A membrane is disposed between the conductive walls on the base. An electric field is propagated between the conductive walls in the plane of the membrane. The electrically insulative base has one or more through holes between the electrically conducting walls where the membrane is disposed.

The chip is placed inside a container (e.g., made of silicon based wafer) and base and can have surrounding walls. A well is formed (e.g., by engraving) near the center of the container base directly below the hole or holes of the electrically insulative chip base when the chip is placed inside the container. At least one passageway is formed (e.g., by engraving) in the container base and extends from the well to the outside. A conduit may extend in each passageway. A third electrode is fabricated on the bottom of the well. An electrically conductive pad extending from the electrode in the well to the wall is fabricated on the container base.

This invention relates to probing structural changes of the membrane and the functions associated with them as an in-plane transverse electric field is applied between the conductive walls of the chip, using electric current measurements, impedance gain phase analysis, raster scanning by atomic force microscope (AFM), and observation with confocal, fluorescence or other microscopes, x-ray and nuclear magnetic resonance (NMR), but not limited to these tools.

The invention enables probing of cellular processes such as structural changes of proteins, channeling mechanisms, receptor binding mechanisms, protein-protein interactions and interaction of proteins with other molecules, in an environment that mimics an actual living cell membrane. The well represents an interior of a biological cell, and may include various chemical compounds, ions, proteins, RNA, DNA, organelles and various cellular components in a suitable medium while extracellular materials such as ions, ligands and other molecules in a suitable medium can be placed in contact with the top of the membrane. Movement of the electrically charged particles through the membrane and electrical characteristics of individual proteins can be monitored by probing the voltage change across the third electrode and another electrode, for example the electrical conducting tip of an AFM, placed in contact with the exterior fluid, the membrane and individual proteins therein. The conduits extending into the well are used to introduce substances into and out of the well.

The invention can be constructed to facilitate probing multiple cell membranes. More than one pair of electrical conductive walls can be fabricated side-by-side on the electrical insulative base with one or more through holes between the electrical conductive walls for each of them. These pairs can be separated from each other by electrically nonconductive walls so that different extracellular materials and other molecules can be placed in each of them. These pairs can be electrically connected in series or parallel so that the membranes can be subjected to the same or different voltages (e.g., all cell membranes can receive the same transverse waveforms at the same time in case of parallel connection). The container can have multiple wells isolated from each other accessible by individual through holes in the chip base or a single well accessible by multiple through holes of the chip base. This aspect of the invention permits the use of one or more cell membrane as controls while the other identical cell membranes are subjected to various experimental conditions.

The embodiments of the invention include a combination of a chip and container for the chip, an apparatus and a method for probing conformational changes of a membrane and the functions associated with them by applying a transverse electric field in the plane of the membrane. Referring to the first embodiment, a chip includes a base. Electrically conductive walls can be spaced apart from each other and fabricated on the base. The base and the conductive walls form a containment region that is configured to receive a membrane. The membrane has opposing surfaces. An interior plane is bounded by the membrane surfaces and extends along the membrane. The base is comprised of an electrically insulative material in the containment region adapted to support at least one of the membrane surfaces. One or more through holes are made in the non-conductive base in the area between the conductive walls preferably near the middle of the containment region. The conductive walls extend to a height above the base that is at least as large as a thickness of the membrane and, in particular, approximates the membrane thickness.

One way of constructing the inventive chip is to use a flat, thin wafer of a silicon-based electrically insulative material as the base. This base can be flat across the entire side where the conductive walls are located. On the other hand, the base can be designed to be flat in the containment region and to have other contours outside of the containment region. One particularly suitable design is to fabricate the conductive walls directly on the flat wafer. One or more through holes are made in the wafer in the area between the conductive walls preferably near the middle of the containment region.

The container that receives the chip can include at least two surrounding walls and has a base made of an electrically insulative material. A well is formed such as by engraving near the center of the container base. This well is positioned below the membrane when the chip is placed in the container. An electrode can be fabricated on the surface of the bottom of the well and does not extend the depth of the well. An electrically conducting pad can be fabricated on the base of the container and extends from the electrode in the well onto an adjacent container wall. At least one conduit is disposed in the container and extends from the well through the base to the outside.

One way of constructing the container is to use a flat, thin wafer of a silicon-based electrically insulative material as the base and the walls. The container base is fabricated such that one or more wells are fabricated in the base. This base can be flat across the entire side. On the other hand, the base can be designed to be flat outside and inside the wells. An electrode flat and not extending the depth of the well is fabricated on the surface of the bottom of the well. An electrically conducting pad extending from the electrode in the well is fabricated on the base of the container. Two conduits extending from the well through the base to the outside is fabricated in the container.

Referring to the second embodiment an apparatus comprises the chip and container described above, an electrical power source for applying an electric field between the conductive walls, and an instrument adapted to probe or image the membrane. The apparatus is adapted to apply an electric field between the conductive walls along the plane of the membrane.

The term "in-plane electric field" is defined herein to mean an electric field in a direction along a plane in the interior of the membrane that extends along (i.e., generally parallel to) the membrane surfaces. Reference in this disclosure to applying the electric field along the plane of the membrane may not require the electric field direction to be exactly parallel to the surfaces of the membrane. In the case where the membrane is not precisely positioned flat on the base, the electric field may not be propagated exactly parallel to the membrane surfaces and yet this is sufficient for purposes of the invention. It will be apparent to one of ordinary skill in the art that the invention need only refer to one membrane plane as a point of reference to accurately describe application of the in-plane electric field. Reference to the conductive walls having a height approximating a thickness of the membrane means spanning the membrane thickness.

The third embodiment of the invention features a method for probing structural changes in a membrane and functions associated with them by applying an electric field. The chip and container described above are provided, a membrane is positioned between the conductive walls in contact with the chip base and traversing the through hole; a first material is added on top of the cell membrane; a second material is inserted through the passageway into the well; and an electric field is applied between the conductive walls along the plane of the membrane.

In view of the use of the present invention with biological cell membranes and biological cells, the chip and the container can be sterilized, dried with an inert gas, and packaged in a sterile condition. Each chip is disposable after being used for one membrane while the container can be reused.

Specific features of the invention will now be described. The apparatus for imaging or probing the membrane includes an instrument selected from the group consisting of an atomic force microscope, a confocal microscope, a confocal laser scanning microscope, a flourescence microscope, X-ray spectrometer, NMR impedance gain phase analyzer, and combinations thereof. The apparatus includes an instrument adapted to determine the properties of the membrane, including topographical, electrical, viscous, and elastic properties.

As defined herein the membrane can be a bilayer comprised of amphiphilic lipids, cholesterols, proteins, a part of a cell membrane, and combinations thereof. The membrane can include constituents selected from the group consisting of glycolipids, phospholipids, cholesterol, proteins, and combinations thereof.

In particular, the height of the conductive walls approximates the thickness of the membrane, e.g., the monolayer, bilayer or cells as described above. The invention contemplates using conductive walls having heights greater than the membrane thickness so long as this does not significantly interfere with application of the in-plane electric field. In particular, the membrane can extend to a height of not more than 10 nanometers from the base, specifically, ranging from 5 to 10 nanometers. The spacing between the conductive walls is selected to be sufficient to accommodate the membrane sample being probed and use of an electric field of an appropriate magnitude and in particular, can be not more than 10 micrometers and in particular from 3 to 10 micrometers. The chip base and its conductive walls can be configured whereby the walls extend perpendicular to the base and parallel to each other. The base can be flat in a containment region located between the conductive walls where the membrane is disposed. In one aspect of the invention there is no cover over the containment region. This enables insertion of membrane constituents and other substances or articles, which can be used or whose effect on structural transitions can be probed by application of the in-plane electric field.

The topmost surface of the membrane located in the containment region can be contacted with an electrode such as a tip of an Atomic Force Microscope ("AFM"), forming an electric field between the tip and the third electrode in the well. This advantageously permits applying a field to individual molecules in the membrane, such as to an individual protein, perpendicular between the tip and the third conductor. The tip of the AFM can be moved to apply the electric field one at a time to a plurality of proteins in contact with the membrane.

The voltage source used in the apparatus is adapted to apply direct or alternating voltage along the plane of the membrane. The voltage source can apply voltage pulses in the form of square or triangular pulses, sine wave, or other form of pulses. An electrical resistor can be connected to an electrical lead extending from the voltage source and to one of the conductive pads of the conductive walls. Another electrical lead from the other conductive wall is connected to the voltage source. A voltage drop across the resistor is monitored using an oscilloscope while varying the electric field applied along the plane of the membrane.

Referring to specific aspects of the method, in one technique the cell membrane can be contacted with a protein (e.g., the protein can be inserted in the membrane). The electric field is applied along the plane of the cell membrane and the effect of the electric field on the protein is monitored. Proteins that span the membrane, such as transmembrane proteins, proteins that have residues extending in the membrane, or proteins that are bound or interact with other proteins or molecules that contact the membrane, can be investigated using the present invention. For example, the investigated protein can contact at least one molecule, and that molecule can directly contact the cell membrane. Alternatively, that molecule can contact another molecule that directly contacts the cell membrane. The method includes monitoring an effect of the electric field on a constituent of the cell membrane selected from the group consisting of a receptor protein, channel proteins and combinations thereof.

In one technique the cell membrane can be contacted with a protein (e.g., the protein can be inserted in the membrane). The electric field is applied along the plane of the cell membrane and the effect of the electric field on the protein is monitored. Transportation of elements such as ions and small molecules from one side of the membrane to the other side can be investigated by using the present invention. The binding of proteins and other molecules to the transmembrane proteins can be investigated by the present invention.

Various techniques may be used to position the membrane in the containment region. It is desirable to achieve precise alignment of the lower membrane surface on the base and the ends of the membrane in contact with the conductive walls. In one technique, the membrane is positioned on the base in the containment region by filling liquid in the containment region, forming the membrane on the surface of the liquid, and subsequently evaporating the liquid causing the membrane to dispose on the base in the containment region over the through hole or holes. In another technique the membrane is positioned on the base in the containment region by immersing the chip in a liquid, forming the membrane on the surface of the liquid, lifting the base from the liquid causing the liquid to leave the containment region, and causing the membrane to depose on the base in the containment region over the through hole or holes.

The present invention offers numerous advantages. The invention enables probing of membranes by applying the transverse in-plane electric field, which heretofore was not possible. The invention permits investigating membrane systems on the scale of a monolayer or bilayer, which will uncover behavior that may not be observable in bulk. One particularly valuable aspect of the invention is its ability to analyze the cell membrane. Various cell membranes can be used from various cell and tissue types, conditions and environments. This can be done with extreme versatility. The membrane can be formed so that its composition is known. The specific lipids can be extracted and purified from existing membranes and used in the sample membrane. Specific proteins can be inserted one at a time at particular locations in the membrane. These proteins can be inserted at isolated locations or at locations near other proteins to enable probing of their interaction. On the other hand, the invention offers the flexibility of designing the sample membrane with a plurality of proteins. The membrane can be made to include a variety of different proteins and other membrane constituents. The sample membrane can be a portion of an actual biological cell membrane.

The membrane can be probed in a variety of ways. Because the containment region can be without a cover, the membrane can be physically contacted before, during and after application of the in-plane electric field. For example, the tip of an atomic force microscope can be scanned over the exposed outermost membrane surface in the containment region. Microscopy of the membrane can be carried out, for example, using one or more of these, Atomic Force, Laser Scanning Confocal, and Fluorescent microscopes. The invention enables a thorough evaluation of the various properties of the membrane, including topographical, electrical, viscous, and elastic properties. The membrane also can be positioned so that it can be accessed from one or two sides of the containment region. This offers additional probing, for example, using X-ray spectroscopy.

Not only can changes in the membrane be probed by applying the electric field, but how the constituents of the membrane interact with other molecules and external stimuli can be probed. For example, the membrane can be made to come in contact with including but not limited to: drugs or therapeutics, chemicals, ligands, fluorescence tags, siRNA, antisense RNA, hormones, enzymes, antibodies, viruses, and combinations thereof. For example, one can reconstruct and probe cancer cells and monitor their response to certain molecules of interest, such as anticancer drugs, with and without application of the in-plane electric field. Similarly, one can investigate the capillary endothelial cells of the blood brain barrier and response to certain therapeutics upon manipulation of carriers by applying the in-plane electric field and/or the perpendicular field between the tip of the atomic force microscope and the third conductor. The treatment of the cells can be carried out before, during or after probing of the membrane by application of the in-plane electric field.

The invention can be used to probe the cellular response to external stimuli such as light. The invention can be used to investigate cellular transport. It may be possible to manipulate a protein channel of a membrane in the containment region, to change its conformation from an open conformation to closed conformation. The invention can be used to investigate ligand-receptor binding processes. The binding sites can be identified by scanning the receptor protein with AFM before, during and after a ligand binding to a receptor protein. and the rate of ligand binding can be determined.

The sample membrane can be subject to various treatments and combined with various probing techniques to investigate properties including, but not limited to electric, viscous, elastic, and topographical properties. For example, certain proteins of interest can be fluorescently tagged and then monitored using a fluorescent microscope, while observing their topographical structural transitions using AFM, in response to application of the in-plane electric field. Impedance of the membrane and the electrical characteristics of the membrane can be analyzed to determine the electric, viscous, elastic properties associated with conformational transitions.

It is advantageous for a chip to include a plurality of containment regions isolated from each other by surrounding walls so that multiple experiments can be conducted simultaneously using the chip. The containment regions can be electrically addressed with the in-plane electric field all at the same time by electrically interconnecting the conductive walls of the chip. On the other hand, the chip can be fabricated in a way that enables the containment regions to be electrically independently addressed with the in-plane electric field at different times and different electric fields. One of ordinary skill in the art will recognize that these are but a few examples of innumerable applications of the present invention.

BRIEF DESCRIPTION OF THE DRAWINGS

FIG. 5a,b: Illustrate cross-sectional side views of the inventive container rotated 90 degrees; FIG. 5a being a view as seen along the plane 5a-5a in FIG. 4;

FIG. 5b being a view as seen along the plane 5b-5b in FIG. 4; and FIG. 5a shows the alignment of the inventive chip before being inserted into the container;

FIG. 7b being a view as seen along the plane 7b-7b in FIG. 6; FIG. 7a being without the third electrical conductor or conducting pads on the container for clarity.

DETAILED DESCRIPTION OF THE INVENTION

Referring now to the drawings, an apparatus 10 including a device 12 including a chip 14 and a container 16 into which the chip is received. The chip has an electrically insulating thin wafer as a base 18 on which first and second nano-meter scale electrically conducting walls 20, 22 are fabricated. The wafer has a flat upper or working surface 24. The conductive walls extend perpendicular to the base and are spaced apart approximately parallel to each other by a distance D1. A containment region or volume 26 has a width defined between the conductive walls at distance D1, a height D2 (FIG. 5) defined between the surface of the wafer and upper surfaces of the conductive walls and a length D3 defined by a length of the conductive walls. Electrically conducting pads 28, extending from the electrically conducting walls 20, 22, respectively, are also fabricated on the wafer and can extend to a periphery thereof 32. The height of the pads may be smaller or larger than the height of the conductive walls.

Figure 3:
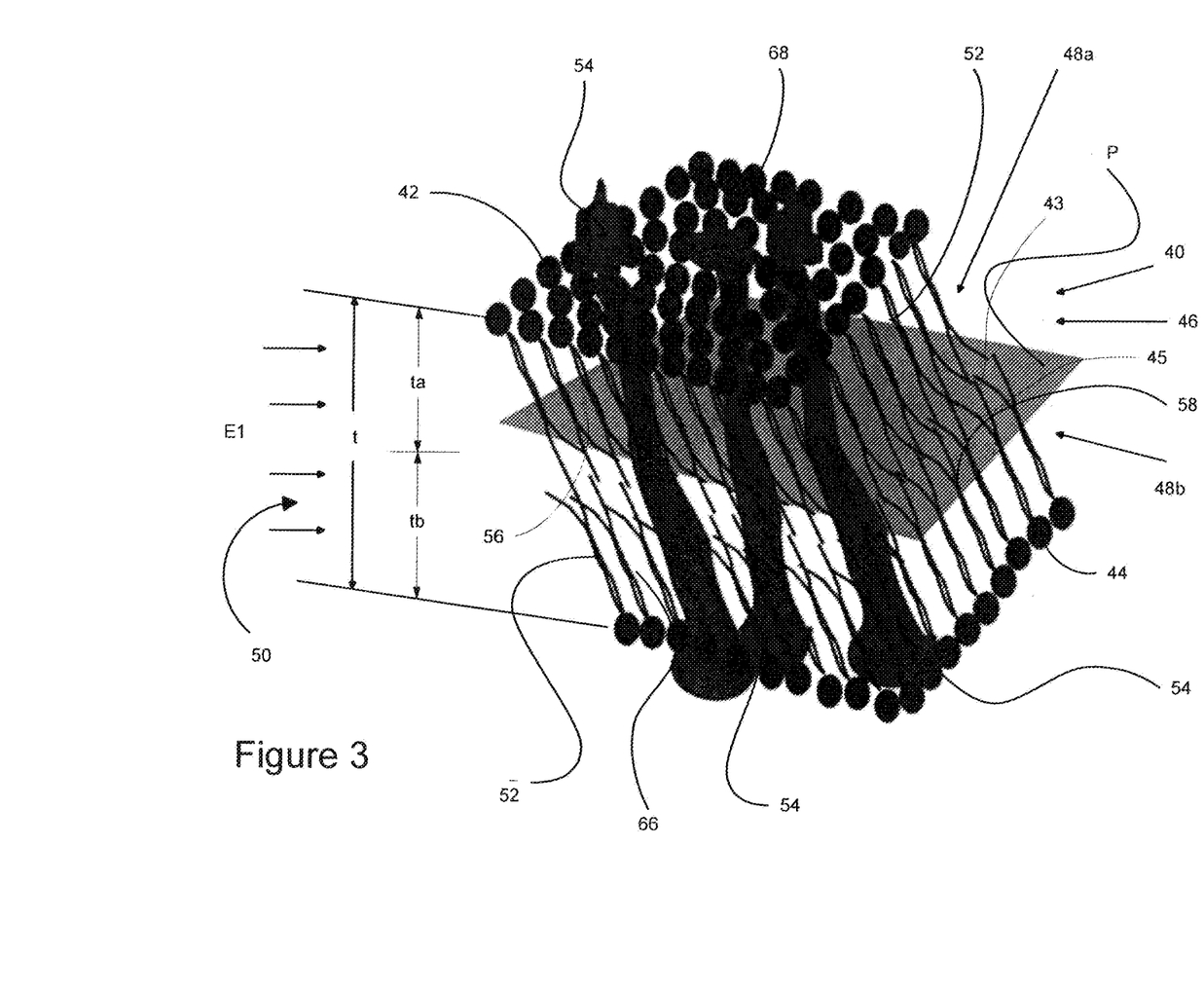
FIG. 3 illustrates a membrane probed in the present invention.

Referring to FIG. 3, a membrane 40 is disposed in the containment region. The membrane composed of a bilayer has opposing spaced apart-surfaces 42, 44 which extend across a major area of the membrane, an interior 46 between these surfaces and a thickness t. An interior plane P of the membrane is bounded by the membrane surfaces and extends along the membrane (i.e., approximately parallel to the membrane surfaces). The membrane can comprise a monolayer 48a or 48b having spaced apart surfaces 42 or 44 and surfaces 43 or 45, an interior between these surfaces and a thickness $t_a$ or $t_b$. The interior plane P of the monolayer would extend between the spaced apart surfaces.

It should be appreciated that certain membranes, as in the case of the biological cell membrane, have an inner membrane surface and opposing, spaced-apart outer membrane surfaces, which may have different localized compositions and concentrations of proteins and other constituents, ion gradients and the like compared to the other membrane surface. The membrane can comprise a monolayer 48a or 48b or bilayer 50 of natural amphiphilic lipids 52 found in the biological cell membrane including glycolipids, phospholipids, synthetic amphiphilic lipids, other constituents of the biological cell membrane including cholesterol and proteins (e.g., a channel protein 54 or a receptor protein), and any combination of them. Moreover, any of these constituents can be added any time after the initial membrane is formed in the containment region. The invention is suitable for probing membranes of any chemical composition, even non-biological membranes. A portion of a biological cell membrane can be deposited in the containment region. An entire biological cell or cells may be deposited in the containment region, which forms the membrane as that term is used in this disclosure. In this case, the electrical conducting walls may be sized and configured to appropriately accommodate the entire cell or cells in the containment region.

The bilayer can be formed by extracting and purifying amphiphilic lipids from biological cell membranes and using these lipids to form the bilayer. Other cell membrane constituents, such as cholesterol and proteins, can be extracted and inserted one or more molecule at a time into the lipid bilayer. The membrane constituents can be inserted into the bilayer before or after application of the electric field. For example, in the case of probing the structural changes of a particular protein of interest (e.g., a channel protein 54 or a receptor protein) one or a limited number of proteins can be inserted and then their response to the in-plane field can be monitored. On the other hand, the membrane can be formed with many proteins, and then the proteins can be monitored in response to the in-plane electric field. The bilayer can be formed by combining one or more chemically or enzymatically synthesized molecules (e.g., lipids).

The electrically conductive walls 20, 22 are fabricated on the chip base or wafer 18 and extend upwardly to a height D2 at least as high as the membrane thickness t, ta or tb in the containment region (i.e., the distance between the membrane surfaces in a direction perpendicular to the base). In particular, the conductive walls can have a height D2 that approximates the thickness t, $t_a$ or $t_b$ of the membrane (FIG. 5), for example, a height in a range of 5 to 10 nanometers from the surface of the conductive wafer. The membrane can have a height D2 approximating the thickness of a molecular monolayer or bilayer and, in particular, the thickness of a biological cell membrane, or biological cell or cells when positioned in the containment region. The distance D1 between the conductive walls can vary as desired depending on the sample. For example, the distance is in a range of about 3 to 10 micrometers. The chip includes at least one through hole 60 that can be centered between the conductive walls in the containment region. The membrane 40 deposed in the containment region extends over the through hole.

The containment region 26 advantageously is exposed or uncovered on the top and in particular, on one or two sides 62, 64 as well. An advantage of the invention is that it enables probing of the top surface of the membrane and, optionally, sides of the membrane. In addition, the open top of the containment region permits adding any component to the membrane before, during and after application of an electric field, including but not limited to membrane constituents. When the membrane 40 is positioned in the containment region, the lowermost membrane surface 44 is in contact with surface 24 of the wafer and covers the opening 60 while the opposing topmost membrane surface is exposed to probing. The wafer provides stability of the membrane in the containment region while the portion of the membrane extending over the opening permits passage of material upwards and downwards into or through the membrane. Two sides of the membrane (e.g., sides 56, 58) are in contact with the conductive walls 20, 22. One or both of the other sides of the membrane 66, 68 can also be exposed to probing near open sides of the containment region 62, 64 of the chip.

Figure 4:
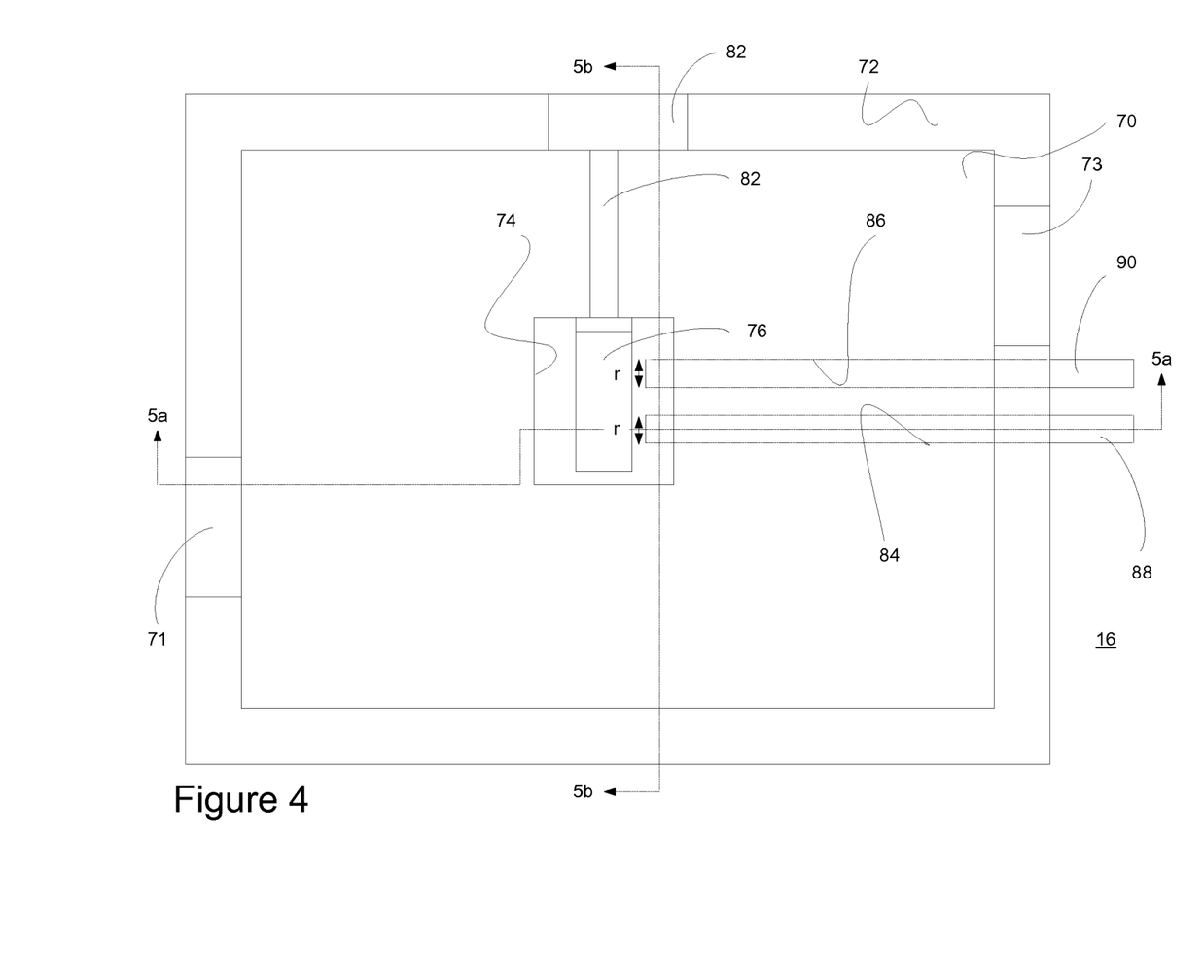
FIG. 4: Illustrates a configuration of the inventive container for the chip in a top view.
Figure 5A:
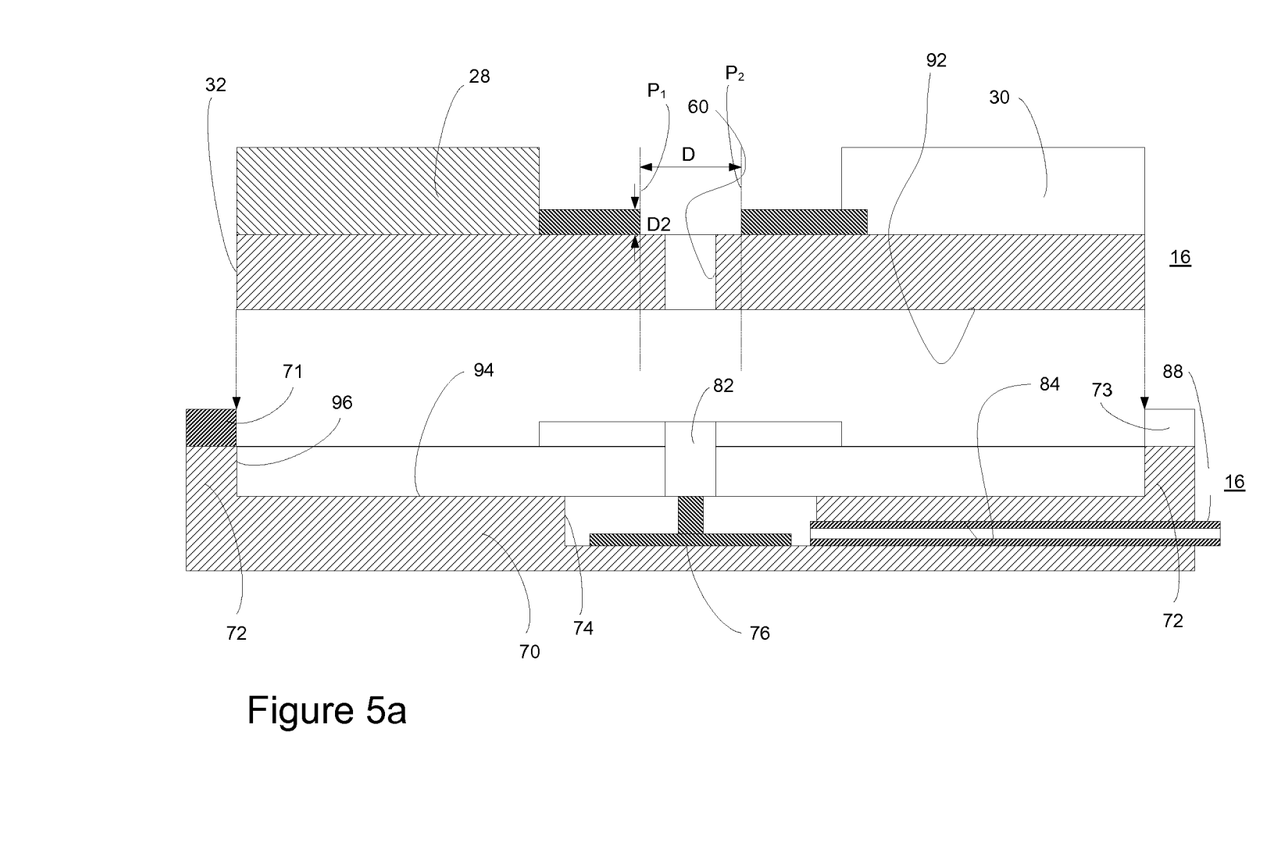
Figure 5B:
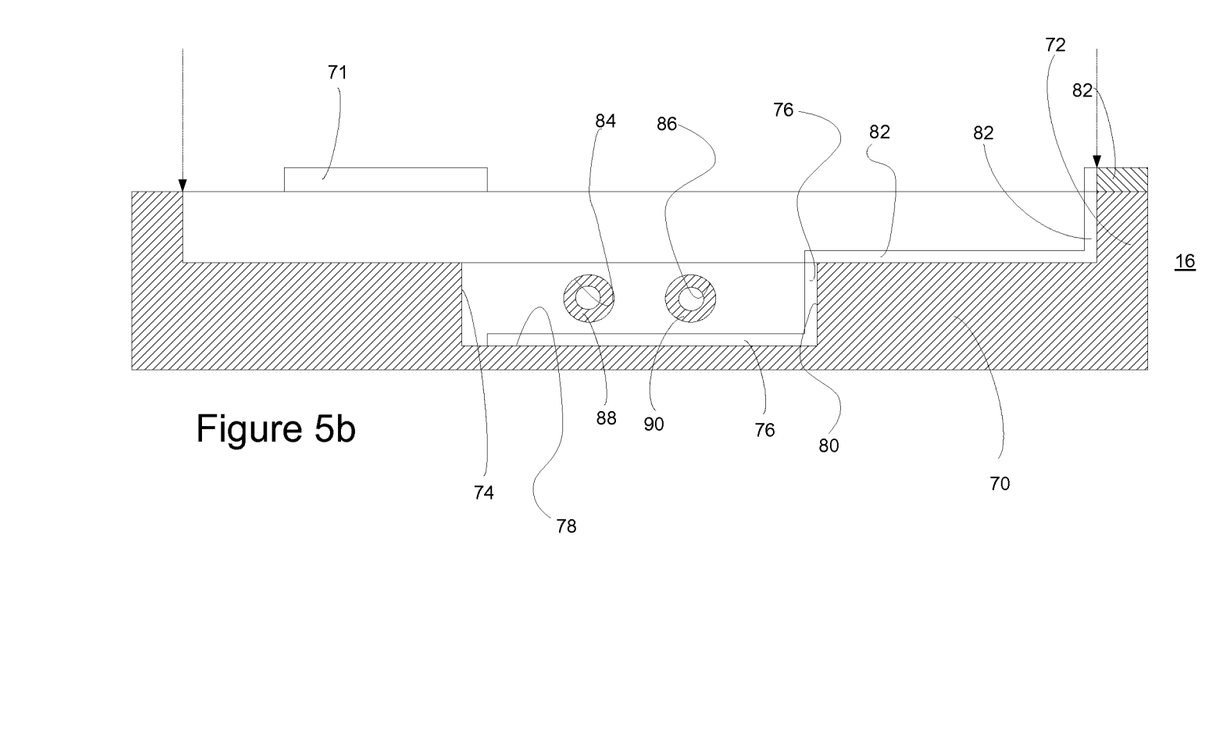
Figure 6:
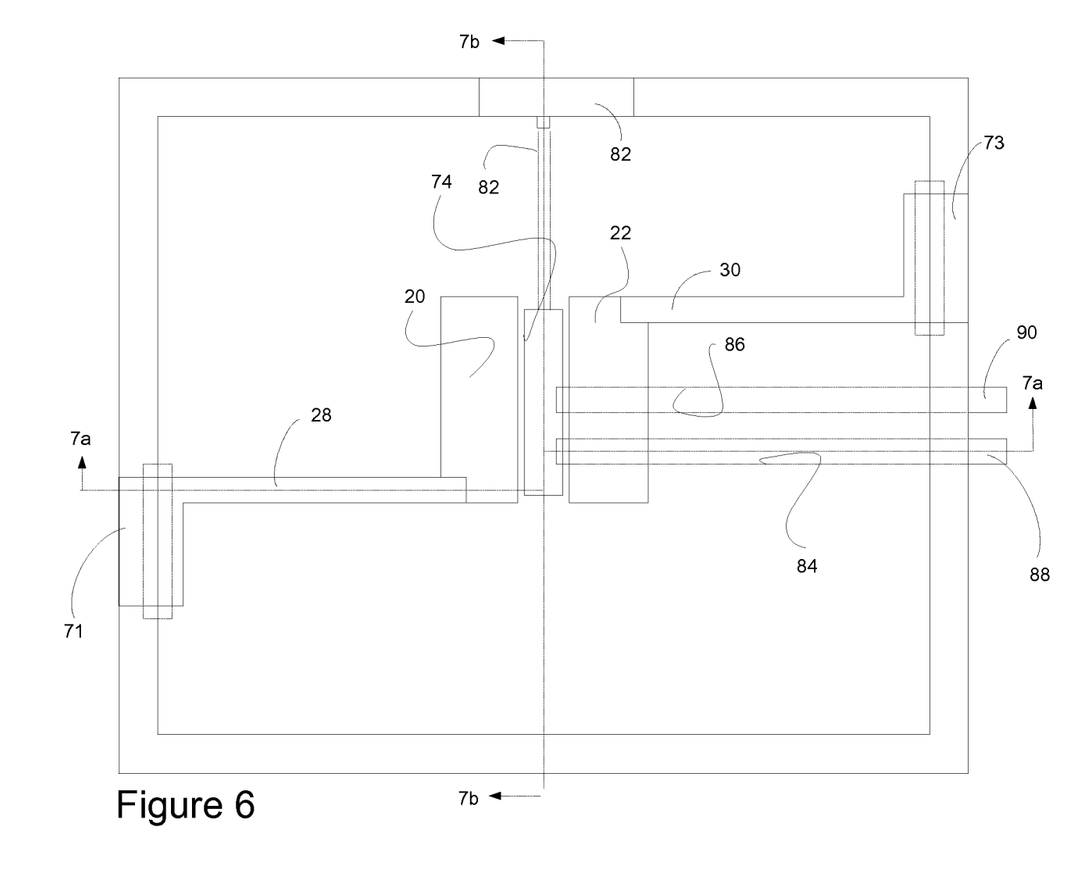
FIG. 6: Illustrates a top view of the inventive device including the chip received in the container.

Referring to FIGS. 4 and 5, the container 16 includes an electrically insulative base 70 and wall 72 extending around the periphery thereof. The wall 72 can completely surround the container base or can extend on only two opposite sides thereof. First and second conducting pads 71, 73 are disposed on the container walls in alignment with the pads 28, 30.

The container base includes a well 74 centered beneath the through hole 60 and the containment region of the nanochip. A third electrode 76 is fabricated in between a plane P1 of the inner surface of the first conducting wall and a plane P2 of the surface of the second conducting wall (FIG. 5), on the floor 78 of the well beneath the containment region and on a side wall 80 of the well. The third electrode 76 is spaced from the conductive walls so as to be electrically isolated therefrom. Electrical conducting pad 82 is fabricated on the container wall, and on the container base into contact with the third electrode 76. Ingress and egress passageways 84, 86 extend from an exterior surface of the container to the well 74. Each passageway includes a conduit or needle 88, 90 disposed therein.

The bottom of the chip base 92 contacts the upper base surface 94 of the container (FIG. 5). The perimeter of the chip base 32 contacts the inside surface 96 of the container walls. This contact between chip and container establishes an electrical connection between the conductive pads 28, 30 of the chip and electrodes 71, 73, respectively, fabricated in alignment with the pads on the container wall 72.

The first conducting wall, second conducting wall, pads on the chip, third electrode and pads on the container and container wall, can be made of any electrical conducting material, for example, Au, Ag or Cu but not limited to these. The wafer and container can be made of non electrical conducting materials, for example, $Si/SiO_2$ but not limited to these.

Figure 8:
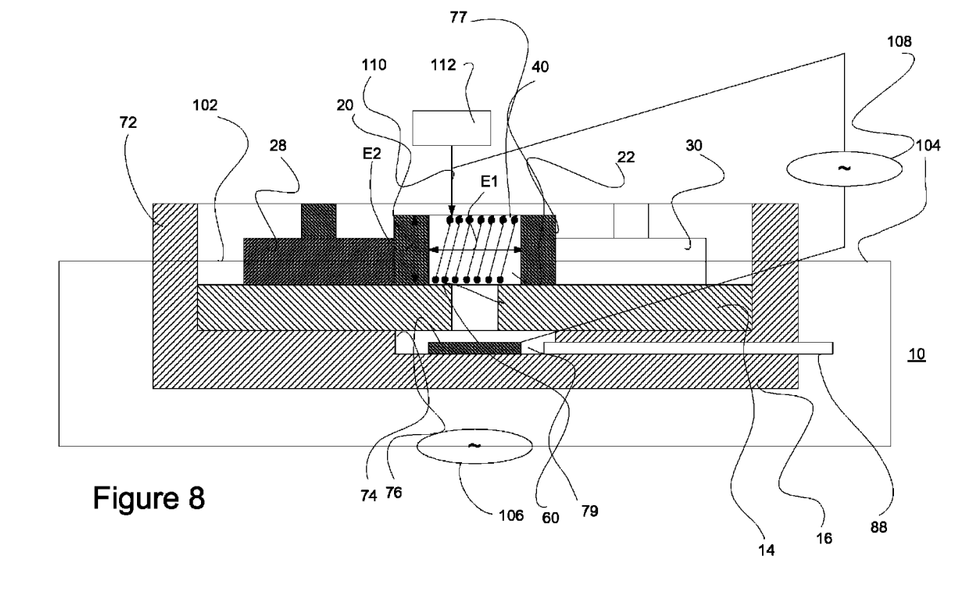
FIG. 8: Illustrates a cross-sectional side view of the inventive device similar to the view shown in FIG. 7a, with membrane and application of first and second voltage sources to the membrane.

Various extracellular or outer components, natural or synthetic, in a suitable medium, or other components that would be apparent to one skilled in the art in view of this disclosure, (77) can be disposed on top of the membrane when it extends over the through hole (FIG. 8). Various inner cellular or inner components, natural or synthetic, in a suitable medium, or other components that would be apparent to one skilled in the art in view of this disclosure, (79) can be fed into the well though ingress 84 and can be extracted from the well through a egress 86. Examples of suitable extracellular components are ions and ligands. Examples of suitable inner cellular components are components selected from the group consisting of RNA, DNA, proteins, ions, cell organelles and combinations thereof. Suitable mediums include water, and various natural or synthetic buffers. The membrane components and inner and outer components and mediums may establish any ion gradients across the membrane that are desired, such as those exhibited by certain membranes in their particular biological environment.

Figure 1:
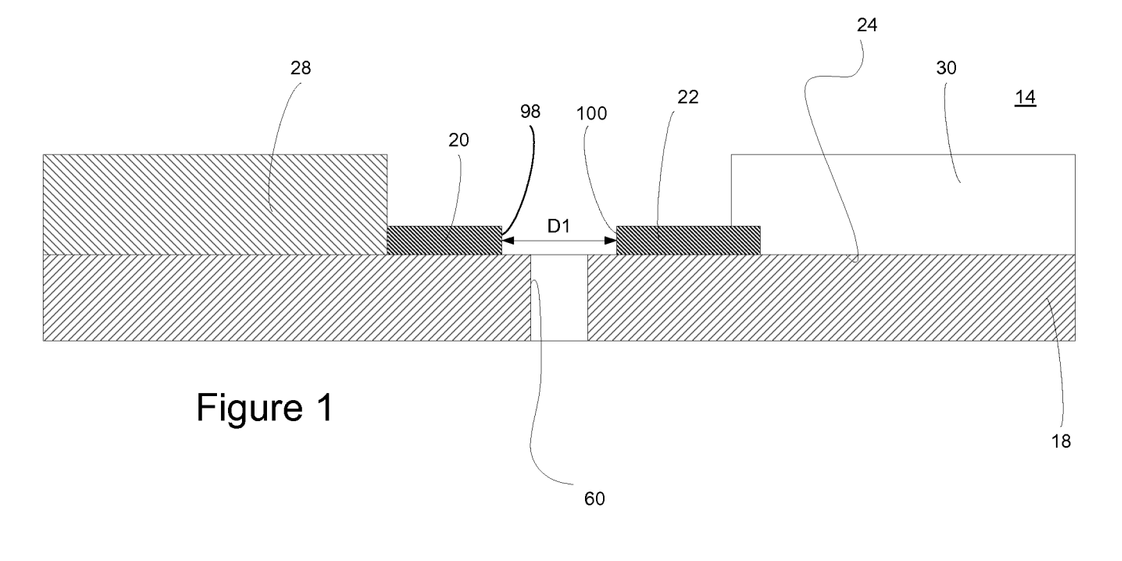
FIG. 1: Illustrates a configuration of the inventive chip in a cross-sectional side view as seen along the plane 1-1 in FIG. 2.
Figure 2:
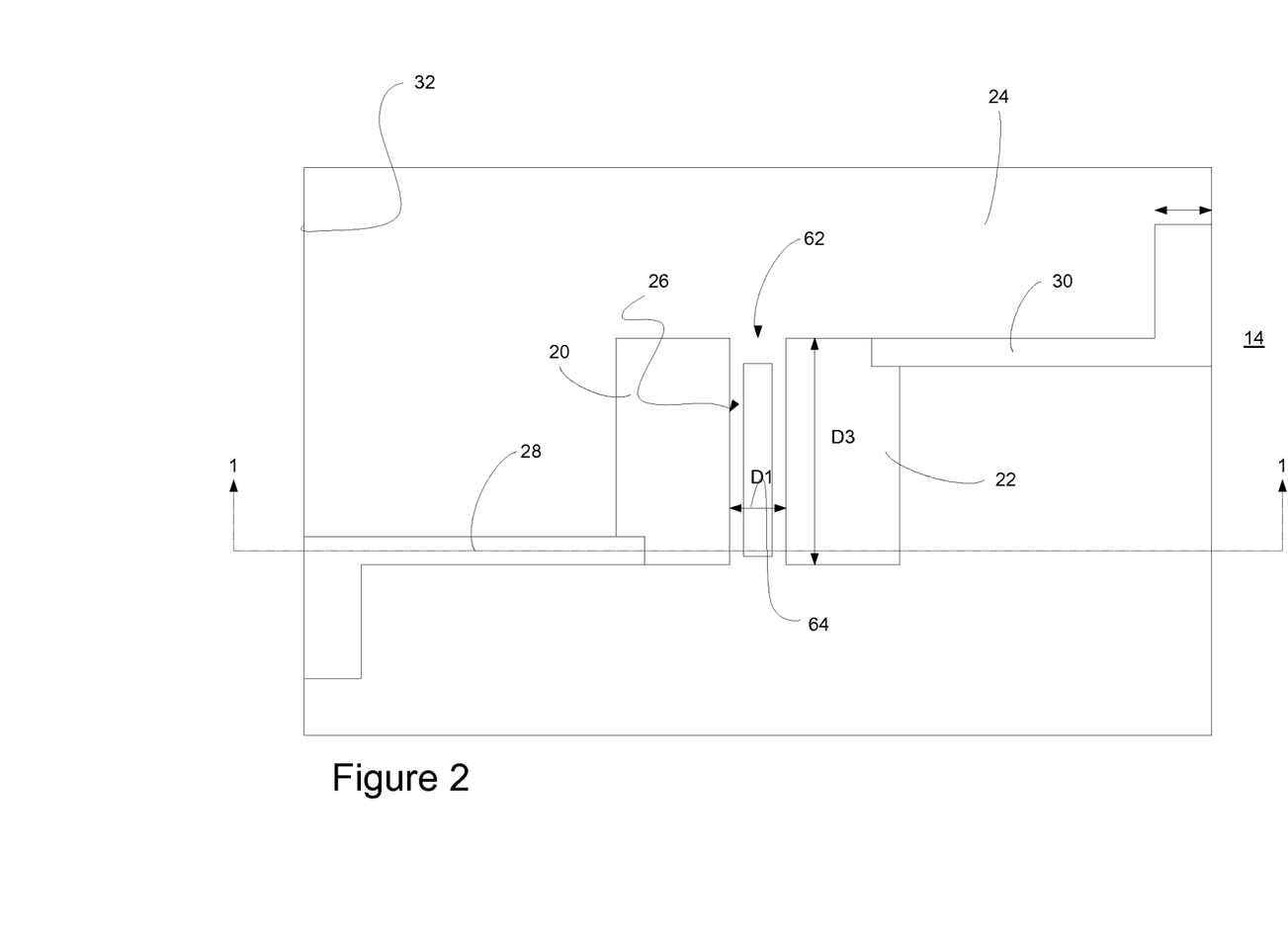
FIG. 2: Illustrates a top view of the chip of FIG. 1.
Figure 7A:
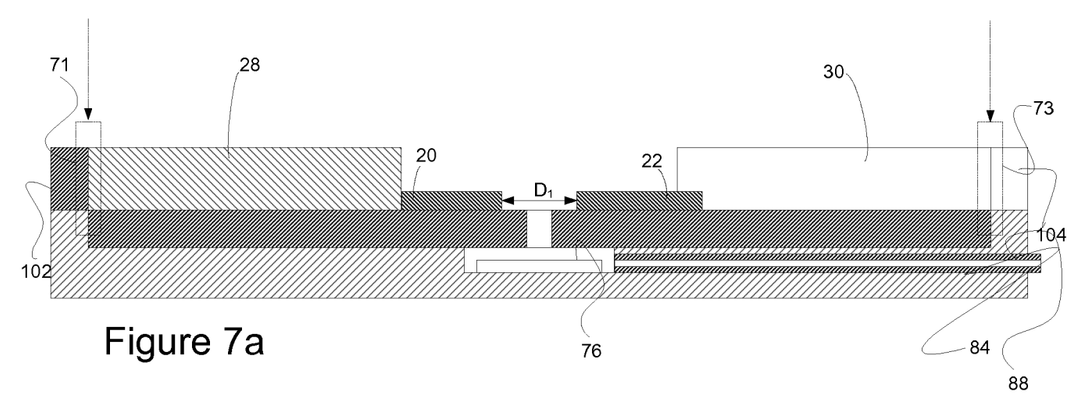
FIG. 7a, b: Illustrate cross-sectional side views of the device of FIG. 6 rotated 90 degrees, FIG. 7a being a view as seen along the plane 7a-7a in FIG. 6.
Figure 7B:
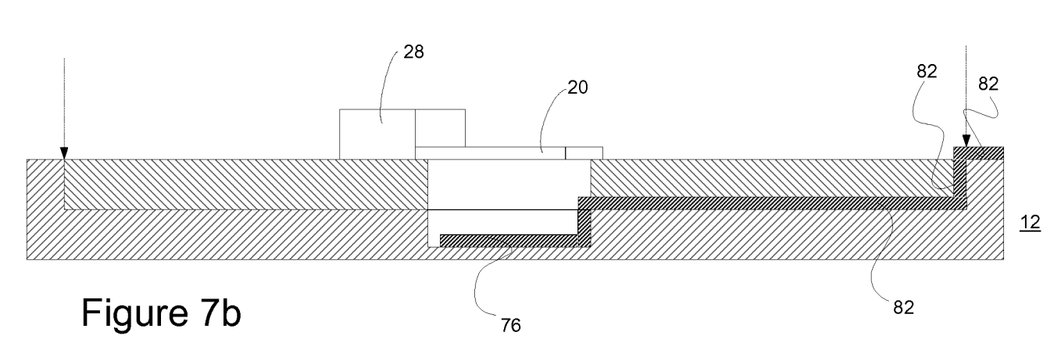

Referring to FIGS. 1 and 3, a first voltage source applies an electric field E1 along the plane P of the membrane 40 when it is positioned so that the bottom surface 44 is disposed on the wafer and the membranes sides 56, 58 contact inner surfaces 98, 100 of the conductive walls. It is desirable to position the membrane flat on the wafer. This assists in probing the exposed top surface 42 of the membrane at a known location. In addition, as the conductive walls are perpendicular to the wafer, the electric field E1 can be applied along the plane of the membrane P. Electrical leads 102, 104 from a voltage source 106 (FIG. 8) are connected to the electrical conducting pads 28, 30, respectively, enabling application of a voltage to the conductive walls that propagates electric field E1 between the electrically conducting walls in a direction that is perpendicular to them along the plane P of the membrane when the lower membrane surface is disposed flat on the wafer in the containment region. Alternatively, if the conductive pads 28, 30 extend to the periphery of the chip as in FIG. 7a and conducting pads 71, 73 are fabricated on the wall of the container, making an electrical connection therebetween, the voltage can be applied by leads 102, 104 to the conductors 71, 73 on the wall of the container to propagate the electric field E1 along the plane of the membrane.

A second voltage source 108 can apply a voltage to the third electrode or not. An electric field E2 may thus be established in the membrane between an electrode 110 such as the tip of the atomic force microscope in contrast with the membrane (represented by an arrow in FIG. 8) and the third electrode. This electric field E2 may extend in a direction perpendicular to the base.

The first and second voltage sources may apply a direct or alternating voltage parallel to or perpendicular to the plane P of the membrane, respectively. The voltage sources can apply voltage pulses, for example, square pulses, triangular pulses, and sine wave. The amplitude and the frequency of the voltage pulse can be selected by one of ordinary skill in the art in view of this disclosure. The voltages will be applied at suitable magnitudes for causing structural changes to the constituents of the membrane.

Structural transitions in the membrane and the proteins embedded in or in contact with the membrane are caused by the reorientation of the membrane molecules coupled to the in-plane electric field. Structural changes to the membrane in response to application of the in-plane electric field are probed by electric current measurements, atomic force microscope, confocal microscope, fluorescent microscope and X-ray spectrometer, but not limited to these tools. Viscous, elastic and electric properties of the membrane can be measured in accordance with the invention.

One particularly suitable instrument of the inventive apparatus for probing the bilayer is an Atomic Force Microscope 112 ("AFM") (FIG. 8), which is capable of detecting structural changes taking place in the constituents of the membrane. The atomic force microscope and other spectroscopic instruments are able to determine the structure of the membrane through the open top or sides before, during, and after an electrical field is applied in the device. Of course, while the open surfaces of the containment region is an advantageous feature of the present invention, one of ordinary skill in the art will appreciate in view of this disclosure that a cover for the open top or sides of the containment region is desirable in some instances. For example, a cover (e.g., glass or plastic coverslip) might be placed on top of the conductive walls before, after, and in some cases during, microscopy to prevent any contamination or to prevent drying of the membrane. Certain constituents of the membrane and the cells may be fluorescently labeled and can be viewed through a cover using a fluorescent microscope while an electric field is applied in the device.

The inventive chip can include one or more containment regions 26. The first voltage source 106 can electrically address the conductive walls of each containment region with the same or different voltage magnitudes and times. In addition, the voltage source 106 can apply voltage to containment regions on different chips at the same time. The membranes 40 that are positioned in the multiple containment regions can be the same or different, for example, some containment regions of a chip including bilayers or monolayers, other containment regions of the chip including cells, and still other containment regions of the chip including cell membranes, or all containment regions of the chip including cell membranes but from different cell or tissue types or subject to different treatments. Each container can have one or more wells that each communicates with numerous through holes in a chip or wells that are each isolated from each other and each communicate only with one through hole of the chip.

Many modifications and variations of the invention will be apparent to those of ordinary skill in the art in light of the foregoing disclosure. Therefore, it is to be understood that, within the scope of the appended claims, the invention can be practiced otherwise than has been specifically shown and described.

What is claimed is:

1. A device for probing changes in a membrane by applying an in-plane transverse electric field, comprising:
    a flat chip base including electrically conductive walls disposed on the chip base, the conductive walls approximately perpendicular to the chip base and having a height above said chip base of not more than 10 nanometers;
    a containment region formed between the walls and the chip base, the containment region operative to receive the membrane such that the membrane spans the entire containment region and a plane of the membrane lays perpendicular to the sides of the conductive walls;
    a through hole in the chip base which opens to an enclosed well attached to the chip base and located below the through hole;
    a first material on top of the received membrane and a second material within the enclosed well;
    a voltage source configured to apply an in-plane electric field along an internal reference plane extending through the received membrane; and
    wherein the received membrane is selected from the group consisting of: a monolayer or bilayer comprised of amphipathic lipids, a cell membrane, a molecular bilayer, a molecular monolayer, a non-biological membrane, and combinations thereof, and the membrane is positioned by the containment region such that the internal reference plane is a transverse plane which divides the membrane into top and bottom membrane surfaces and is generally parallel to the flat chip base.

2. The device of claim 1, wherein said first material is selected from the group consisting of ions, ligands and combinations thereof.

3. The device of claim 1, wherein the second material comprises components selected from the group consisting of RNA, DNA, proteins, ions, cell organelles and combinations thereof.

4. The device of claim 3, wherein said protein is selected from the group consisting of a receptor protein, a membrane transport protein, a transmembrane protein, an ion channel and combinations thereof.

5. The device of claim 1, wherein said voltage source configured to apply said electric field applies said electric field to said membrane as voltage pulses.

6. The device of claim 5, wherein said electric field is provided by AC voltage pulses.

7. The device of claim 5, wherein said electric field is provided by DC voltage pulses.

8. The device of claim 5, wherein said voltage pulses are selected from the group consisting of square pulses, triangular pulses, and sine wave.

9. The device of claim 1, wherein said membrane includes constituents selected from the group consisting of glycolipids, phospholipids, cholesterol, proteins, and combinations thereof.

10. An apparatus comprising said device of claim 1 and a second device that monitors a response of said membrane to said electric field applied along the plane of said membrane.

11. The apparatus of claim 10, wherein said second device that monitors the response of said membrane to said electric field includes an atomic force microscope having an electrically conductive tip, a third electrode being provided on a lower surface of said well, wherein electrical conduction is established between said conductive tip and said third electrode.

12. The apparatus of claim 10, wherein said second device that monitors the response of said membrane to said electric field is selected from the group consisting of: atomic force microscope, confocal microscope, laser scanning confocal microscope, scanning electron microscope, transmission electron microscope, phase contrast microscope, differential-interference-contrast microscope, dark-field microscope, bright-field microscope, electron microscope tomography, fluorescence microscope, X-ray spectrometer, impedance gain phase analyzer and combinations thereof.

13. The apparatus of claim 10, wherein said second device that monitors the response of said membrane to said electric field measures properties of said membrane selected from the group consisting of: topographical, electrical, viscous, elastic, and combinations thereof.

14. The device of claim 1, wherein the top and bottom membrane surfaces are anisotropic.

15. The device of claim 1, wherein the internal reference plane is a substantially flat two-dimensional surface.

16. The device of claim 1, wherein the in-plane electric field allows for changing the conformational state of the received membrane.

17. The device of claim 1, wherein the flat chip base includes a plurality of containment regions, each containment region operative to receive the membrane.

18. The device of claim 17, wherein the plurality of containment regions are electrically interconnected.

19. The device of claim 17, wherein the plurality of containment regions are electrically independently addressable.

20. The device of claim 1, wherein the in-plane electric field allows for probing the conformational state of a monolayer within the received membrane.

21. The device of claim 1, wherein the in-plane electric field allows for probing the conformational state of a bilayer within the received membrane.

* * * * *